United States Patent
Ota

(10) Patent No.: US 12,059,302 B2
(45) Date of Patent: Aug. 13, 2024

(54) ULTRASOUND DIAGNOSTIC APPARATUS, ULTRASOUND DIAGNOSTIC METHOD, NON-TRANSITORY COMPUTER-READABLE RECORDING MEDIUM STORING PROGRAM THEREIN, AND MODEL TRAINING APPARATUS

(71) Applicant: Konica Minolta, Inc., Tokyo (JP)

(72) Inventor: Kazushi Ota, Tokyo (JP)

(73) Assignee: KONICA MINOLTA, INC., Tokyo (JP)

(*) Notice: Subject to any disclaimer, the term of this patent is extended or adjusted under 35 U.S.C. 154(b) by 32 days.

(21) Appl. No.: 17/193,497

(22) Filed: Mar. 5, 2021

(65) Prior Publication Data
US 2021/0275147 A1    Sep. 9, 2021

(30) Foreign Application Priority Data
Mar. 6, 2020 (JP) .................................. 2020-038752

(51) Int. Cl.
| A61B 8/00 | (2006.01) |
| A61B 8/08 | (2006.01) |
| G06N 3/04 | (2023.01) |
| G06N 3/08 | (2023.01) |

(52) U.S. Cl.
CPC .......... *A61B 8/5207* (2013.01); *A61B 8/461* (2013.01); *A61B 8/56* (2013.01); *A61B 8/565* (2013.01); *G06N 3/04* (2013.01); *G06N 3/08* (2013.01); *A61B 2560/0214* (2013.01)

(58) Field of Classification Search
CPC ......... A61B 8/5207; A61B 8/461; A61B 8/56; A61B 8/565; A61B 2560/0214; A61B 8/54; G06N 3/04; G06N 3/08; G06N 3/0454; G06N 3/0472; G06N 3/084
See application file for complete search history.

(56) References Cited

U.S. PATENT DOCUMENTS

| 6,631,474 | B1* | 10/2003 | Cai ..................... G06F 12/0815 |
| | | | 713/320 |
| 8,167,803 | B2* | 5/2012 | McMorrow ......... G01S 7/52038 |
| | | | 600/443 |
| 11,077,320 | B1* | 8/2021 | Hibbard ................ G06T 7/0012 |
| 2009/0043203 | A1* | 2/2009 | Pelissier .................. A61B 8/00 |
| | | | 600/446 |

(Continued)

FOREIGN PATENT DOCUMENTS

| JP | 2019-025044 A | 2/2019 |
| JP | 2020-114294 A | 7/2020 |

OTHER PUBLICATIONS

Office Action dated Jul. 4, 2023 for corresponding Japanese Patent Application No. 2020-038752, and English translation.

*Primary Examiner* — Alexei Bykhovski
(74) *Attorney, Agent, or Firm* — Lucas & Mercanti, LLP

(57) ABSTRACT

Provided is an ultrasound diagnostic apparatus including a transceiver that transmits and receives first ultrasound of a low acoustic output and second ultrasound of a high acoustic output, and a first hardware processor that generates the ultrasound image based on a first reception signal acquired by transmitting and receiving the first ultrasound. The first hardware processor includes a learning model formed of a neural network, and generates the ultrasound image based on an output result of the learning model.

17 Claims, 6 Drawing Sheets

(56) References Cited

U.S. PATENT DOCUMENTS

| | | | |
|---|---|---|---|
| 2009/0105602 A1* | 4/2009 | Gehman | G16H 40/63 600/518 |
| 2014/0323870 A1* | 10/2014 | Satsuka | A61B 8/465 600/459 |
| 2015/0269741 A1* | 9/2015 | Moriya | G06T 7/0012 382/164 |
| 2017/0262982 A1* | 9/2017 | Pagoulatos | A61B 8/469 |
| 2020/0281570 A1* | 9/2020 | Sato | G01S 7/52028 |
| 2021/0244387 A1* | 8/2021 | Washburn | A61B 8/481 |

\* cited by examiner

ULTRASOUND TRANSMISSION
AND RECEPTION SIDE

ULTRASOUND DIAGNOSTIC APPARATUS, ULTRASOUND DIAGNOSTIC METHOD, NON-TRANSITORY COMPUTER-READABLE RECORDING MEDIUM STORING PROGRAM THEREIN, AND MODEL TRAINING APPARATUS

CROSS REFERENCE TO RELATED APPLICATIONS

The entire disclosure of Japanese Patent Application No. 2020-38752 filed on Mar. 6, 2020 is incorporated herein by reference in its entirety.

BACKGROUND

Technological Field

The present invention relates to an ultrasound diagnostic apparatus, an ultrasound diagnostic method, a non-transitory computer-readable recording medium storing a program therein, and a model training apparatus.

Description of Related Art

In the related art, as one of medical image diagnostic apparatuses, there is known an ultrasound diagnostic apparatus that transmits ultrasound to a subject, receives a reflected wave of the ultrasound, and subjects a reception signal to predetermined signal processing, thereby visualizing the shape, properties, or dynamics of the inside of the subject as an ultrasound image. The ultrasound diagnostic apparatus is capable of acquiring an ultrasound image by a simple operation of placing an ultrasound probe on the body surface or inserting the ultrasound probe into the body. and is therefore safe and imposes less burden on the subject.

In recent years, the ultrasound diagnostic apparatus has become more and more compact from the viewpoint of convenience such as portability. For a compact ultrasound diagnostic apparatus, it is important to have such a performance that the compact ultrasound diagnostic apparatus is driven by a battery and can be used for a long time. On the other hand, for acquiring an image quality sufficient for a diagnosis, it is necessary to increase an acoustic output of ultrasound to the maximum extent possible.

Further, in the field of medical imaging apparatus such as a magnetic resonance imaging (MRI) apparatus, a technique for generating an image with high image quality from an image with low image quality by utilizing a learning model trained by machine learning has been developed (for example, see Japanese Patent Application Laid-Open No. 2019-025044). Japanese Patent Application Laid-Open No. 2019-025044 discloses a technique for restoring an image with high image quality from an input degraded image by using a restorer formed of a neural network.

However, a case where an acoustic output of ultrasound is increased often results in a higher transmission voltage as well, which becomes a factor that hinders a reduction in the power consumption and size of an ultrasound diagnostic apparatus. A compact ultrasound diagnostic apparatus needs to be developed while coming to terms with these events contradictory to each other, and requires ensuring a sufficient image quality necessary for a diagnosis even at a low acoustic output.

The technique disclosed in Japanese Patent Application Laid-Open No. 2019-025044 requires a restorer for each classification, has a complicated apparatus configuration, and further needs learning of each restorer so that the learning phase becomes complicated for realizing a highly accurate restorer. In addition, when a set of a degraded image (input data) and a correct image (correct data), which serve as teaching data, is prepared, the degraded image is created from the correct image by performing processing such as undersampling so that the preparation of teaching data before the start of learning is also complicated.

SUMMARY

An object of the present invention is to provide an ultrasound diagnostic apparatus, an ultrasound diagnostic method, a non-transitory computer-readable recording medium storing a program therein, and a learning model training apparatus which are capable of acquiring an ultrasound image with high image quality necessary for a diagnosis even at a low acoustic output and achieving a reduction in the power consumption and size of the apparatus.

To achieve at least one of the abovementioned objects, according to an aspect of the present invention, an ultrasound diagnostic apparatus reflecting one aspect of the present invention is an ultrasound diagnostic apparatus that generates and displays an ultrasound image based on a reception signal corresponding to reflection ultrasound reflected in a subject, the ultrasound diagnostic apparatus comprising:
  a transceiver that transmits and receives first ultrasound of a low acoustic output and second ultrasound of a high acoustic output; and
  a first hardware processor that generates the ultrasound image based on a first reception signal acquired by transmitting and receiving the first ultrasound, wherein
  the first hardware processor includes a learning model formed of a neural network.

To achieve at least one of the abovementioned objects, according to an aspect of the present invention, an ultrasound diagnostic method reflecting one aspect of the present invention is an ultrasound diagnostic method in which a diagnosis is performed with an ultrasound image based on a reception signal corresponding to reflection ultrasound reflected in a subject, the ultrasound diagnostic method comprising:
  transmitting and receiving first ultrasound of a low acoustic output or second ultrasound of a high acoustic output; and
  generating the ultrasound image based on a first reception signal acquired by transmitting and receiving the first ultrasound, wherein
  in the generating, the ultrasound image is generated by utilizing a learning model and based on an output result of the learning model when the first reception signal is input, the learning model being formed of a neural network.

To achieve at least one of the abovementioned objects, according to an aspect of the present invention, a non-transitory computer-readable recording medium storing a program therein, reflecting one aspect of the present invention, is a non-transitory computer-readable recording medium storing therein a program that causes a computer of an ultrasound diagnostic apparatus to execute predetermined processing, the ultrasound diagnostic apparatus generating and displaying an ultrasound image based on a reception signal corresponding to reflection ultrasound reflected in a subject, the predetermined processing comprising:

transmitting and receiving first ultrasound of a low acoustic output or second ultrasound of a high acoustic output; and generating the ultrasound image based on a first reception signal acquired by transmitting and receiving the first ultrasound, wherein in the generating, the ultrasound image is generated by utilizing a learning model and based on an output result of the learning model when the first reception signal is input, the learning model being formed of a neural network.

To achieve at least one of the abovementioned objects, according to an aspect of the present invention, a model training apparatus reflecting one aspect of the present invention is a model training apparatus that trains the learning model to be implemented in the ultrasound diagnostic apparatus, the model training apparatus comprising:

a fifth hardware processor; and a second memory that stores a neural network similar to the learning model, wherein the fifth hardware processor acquires the teaching data.

optimizes an adjustment value of the neural network by using the teaching data, and outputs the adjustment value of the neural network.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

Figure 1:
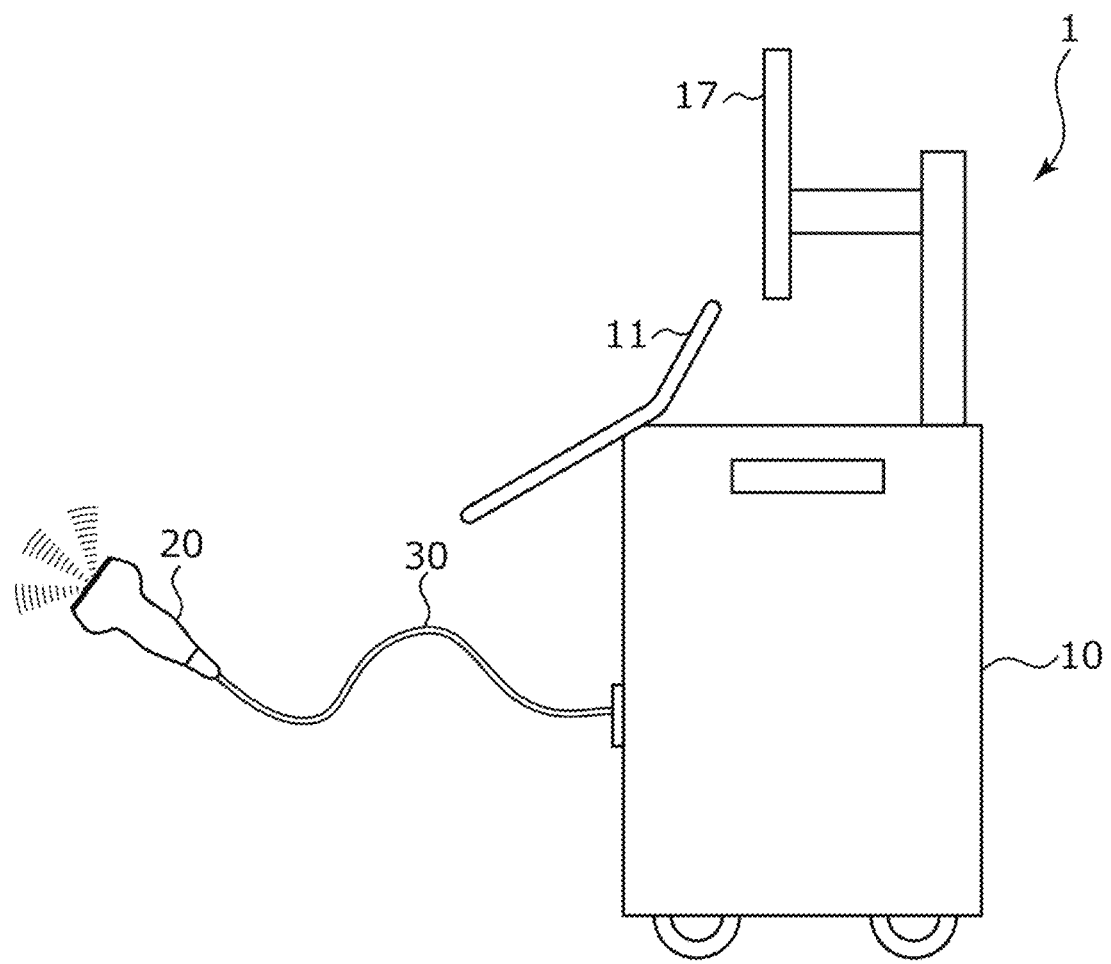
FIG. 1 is an external view of an ultrasound diagnostic apparatus according to an embodiment.
Figure 2:
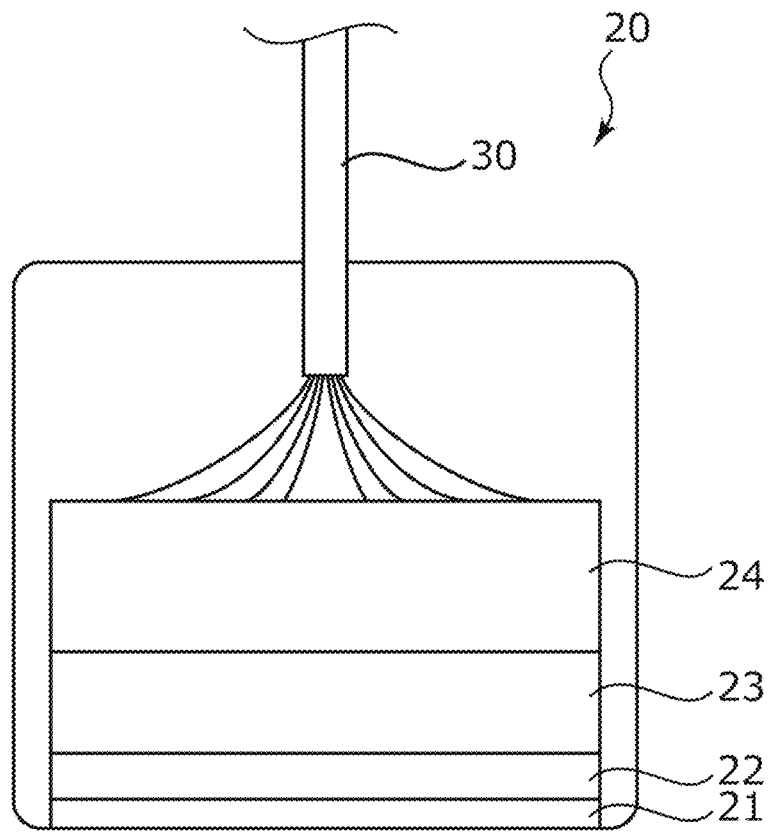
FIG. 2 illustrates a configuration of an ultrasound probe.
Figure 3:
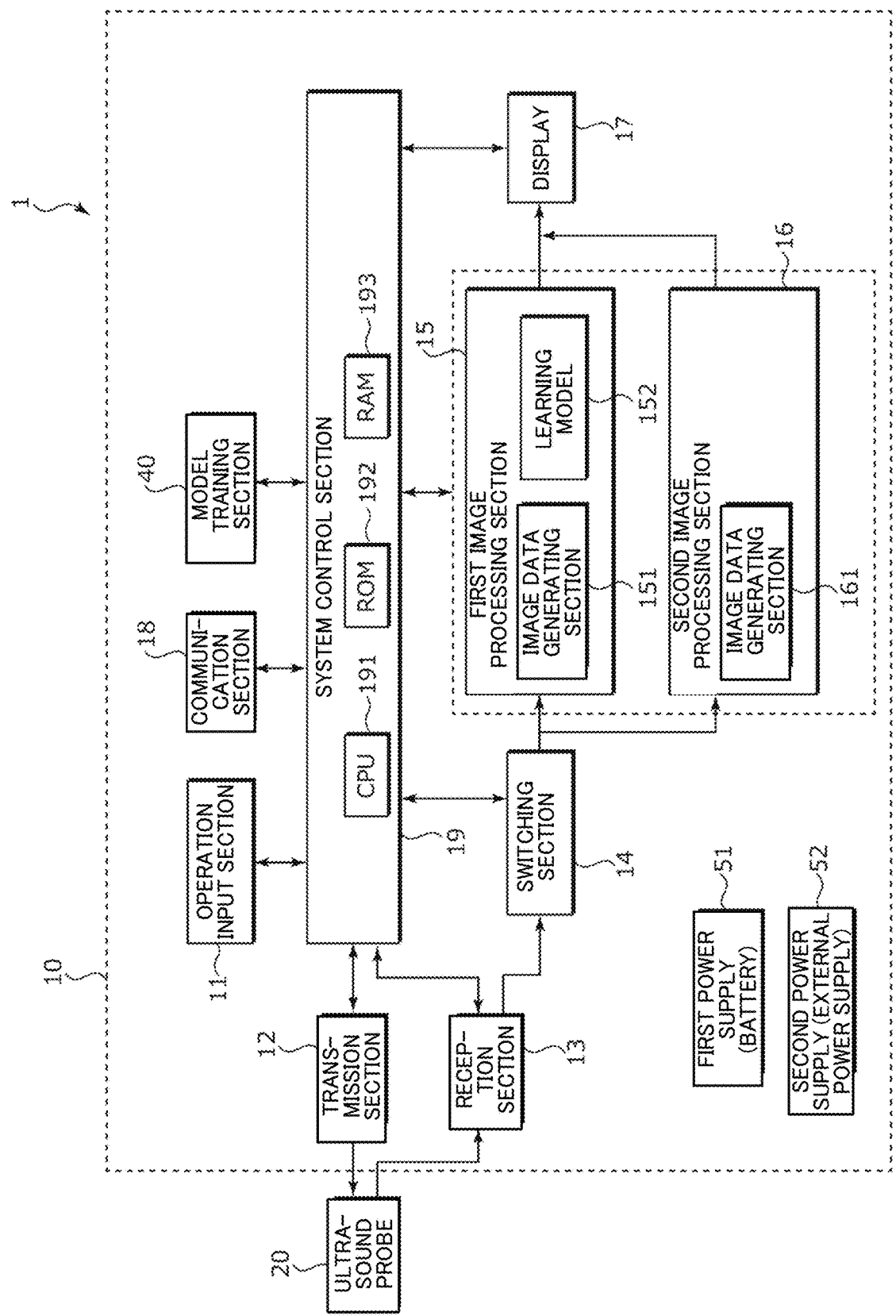
FIG. 3 is a block diagram illustrating a main part of a control system of the ultrasound diagnostic apparatus.

FIG. 1 is an external view of ultrasound diagnostic apparatus 1 according to an embodiment of the present invention. FIG. 2 illustrates a configuration of ultrasound probe 20. FIG. 3 is a block diagram illustrating a main part of a control system of ultrasound diagnostic apparatus 1.

Ultrasound diagnostic apparatus 1 is used to visualize the shape, properties, or dynamics of the inside of a subject as an ultrasound image, thereby performing an image diagnosis.

As illustrated in FIG. 1, ultrasound diagnostic apparatus 1 includes ultrasound diagnostic apparatus main body 10 and ultrasound probe 20. Ultrasound diagnostic apparatus main body 10 and ultrasound probe 20 are connected via cable 30.

Note that, ultrasound probe 20 may be connected to ultrasound diagnostic apparatus main body 10 via wireless communication.

Ultrasound probe 20 transmits ultrasound to a subject, receives an ultrasonic echo (reflection ultrasound) reflected by the subject, converts the ultrasonic echo into a reception signal, and transmits the reception signal to ultrasound diagnostic apparatus main body 10. As ultrasound probe 20, a probe of any electronic scanning system, such as a convex probe, a linear probe or a sector probe, or a probe of a mechanical scanning system, such as a mechanical sector probe, can be applied. Ultrasound probe 20 may include a puncture needle guide section that guides a puncture direction with an attached puncture needle.

As illustrated in FIG. 2, ultrasound probe 20 includes, in the order starting from an ultrasound transmission and reception side, acoustic lens 21, acoustic matching layer 22, transducer array 23, and backing material 24, for example. Note that, a protective layer may be disposed on a surface (ultrasound transmission and reception surface) of acoustic lens 21.

Acoustic lens 21 is a lens that causes ultrasound to converge in a slice direction (a direction orthogonal to a scanning direction in which a plurality of transducers is arrayed). For example, in a case where a material having a slower speed of sound than that of a living body is used for the acoustic lens, the acoustic lens generally has a semicylindrical shape whose central part in the slice direction is protruded.

Acoustic matching layer 22 is an intermediate substance for causing ultrasound to enter a subject efficiently, and matches an acoustic impedance of a transducer (illustration is omitted) and an acoustic impedance of a subject with each other.

Transducer array 23 is formed of, for example, a plurality of strip-shaped transducers arranged in a single row in the scanning direction. That is, ultrasound probe 20 is a so-called single-row probe.

Backing material 24 attenuates unnecessary vibration caused in transducer array 23.

Ultrasound diagnostic apparatus main body 10 visualizes the shape, properties, or dynamics of the inside of a subject as an ultrasound image (B-mode image) by using a reception signal from ultrasound probe 20.

As illustrated in FIG. 3, ultrasound diagnostic apparatus main body 10 includes operation input section 11, transmission section 12, reception section 13, switching section 14 (third hardware processor), first image processing section 15 (first hardware processor), second image processing section 16 (second hardware processor), display 17, communication section 18, system control section 19, model training section 40 (fourth hardware processor), and the like. Each functional block of ultrasound diagnostic apparatus main body 10 is driven by power supplied from first power supply 51 or second power supply 52.

Each of transmission section 12, reception section 13, switching section 14, first image processing section 15, second image processing section 16, communication section 18, and model training section 40 is formed of, for example, a dedicated or general-purpose hardware (electronic circuit) corresponding to each processing, such as a digital signal processor (DSP), an application-specific integrated circuit (ASIC), and a programmable logic device (PLD), and realizes each function in cooperation with system control section 19.

First power supply 51 is formed of a battery, and second power supply 52 receives power supply from an external power supply (AC power supply). In a case where second power supply 52 is connected to the external power supply, second power supply 52 becomes valid, and driving power is supplied by second power supply 52. In a case where second power supply 52 is cut off from the external power supply, on the other hand, first power supply 51 becomes valid, and the driving power is supplied by first power supply 51.

Ultrasound diagnostic apparatus main body 10 has, as operation modes, a low power mode in which the driving power is supplied from first power supply 51, and a normal mode in which the driving power is supplied from second power supply 52. The operation mode is automatically switched according to the state of connection between second power supply 52 and the external power supply, for example.

In the low power mode, first ultrasound of a low acoustic output is transmitted and received in order to suppress the battery consumption of first power supply 51. In the normal mode, second ultrasound of a high acoustic output is transmitted and received in order to acquire an ultrasound image with high image quality.

The transmission voltage of the first ultrasound of a low acoustic output is smaller than that of the second ultrasound of a high acoustic output so that the low power mode consumes less power than the normal mode. On the other hand, in a case where a first reception signal acquired by transmitting and receiving the first ultrasound is image-converted, as it is, to generate an ultrasound image, the image quality of the resulting ultrasound image is low 40) in comparison with that of an ultrasound image to be generated based on a second reception signal acquired by the second ultrasound. In the present embodiment, in a case where the first ultrasound is transmitted and received in the low power mode, enhancement of the image quality of an ultrasound image is achieved by image processing performed by first image processing section 15 in which learning model 152 is implemented. In a case where, for example, a B-mode image is generated by image processing using learning model 152, a B-mode image with high image quality equivalent to that in a case where the second ultrasound is transmitted and received can be obtained from a B-mode image with low image quality.

Operation input section 11 receives, for example, an input of a command to instruct a start of diagnosis or the like, or an input of information on a subject. Operation input section 11 includes, for example, an operation panel including a plurality of input switches, a keyboard, a mouse, and the like. A user can, for example, instruct execution of ultrasound diagnostic processing or instruct training processing of learning model 152 by model training section 40 by using operation input section 11. Note that, operation input section 11 may be formed of a touch screen provided integrally with display 17.

Transmission section 12 generates a transmission signal (driving signal) and outputs the transmission signal to ultrasound probe 20 in accordance with an instruction from system control section 19. Although illustration is omitted, transmission section 12 includes, for example, a clock generating circuit, a pulse generating circuit, a pulse width setting section, and a delay circuit.

The clock generating circuit generates a clock signal for determining the transmission timing and/or the transmission frequency of a pulse signal. The pulse generating circuit generates a bipolar rectangular wave pulse having a preset voltage amplitude at a predetermined cycle. The pulse width setting section sets the pulse width of a rectangular wave pulse that is output from the pulse generating circuit. The rectangular wave pulse generated by the pulse generating circuit is separated into different wiring paths for each transducer of ultrasound probe 20 before or after being input to the pulse width setting section. The delay circuit delays the generated rectangular wave pulse according to the transmission timing of each transducer, and outputs the delayed pulse to each transducer.

Reception section 13 receives a reception signal from ultrasound probe 20 and outputs the reception signal to switching section 14 in accordance with an instruction from system control section 19. Although illustration is omitted, reception section 13 includes, for example, an amplifier, an A/D conversion circuit, and a phasing addition circuit.

The amplifier amplifies, by a predetermined amplification factor set in advance, each reception signal corresponding to ultrasound received by each transducer of ultrasound probe 20. The A/D conversion circuit converts an amplified reception signal into digital data at a predetermined sampling frequency. The phasing addition circuit adjusts the time phase of an A/D converted reception signal by adding a delay time for each wiring path corresponding to each transducer, and performs addition (phasing addition) thereof.)

Switching section 14 appropriately transmits a reception signal from reception section 13 to first image processing section 15 or second image processing section 16 at a stage subsequent to switching section 14 in accordance with an instruction from system control section 19. Specifically, system control section 19 notifies switching section 14 of information on the power supply for supplying the driving power (in the present embodiment, first power supply 51 or second power supply 52). In a case where the power supply for supplying the driving power is first power supply 51, switching section 14 selects first image processing section 15. In a case where the power supply for supplying the driving power is second power supply 52, switching section 14 selects second image processing section 16. Thus, first image processing section 15 is selected in a case where the reception signal is the first reception signal corresponding to reflection ultrasound of a low acoustic output, and second image processing 40) section 16 is selected in a case where the reception signal is the second reception signal corresponding to reflection ultrasound of a high acoustic output.

Note that, information notified by system control section 19 to switching section 14 is not limited to the information on the power supply for supplying the driving power, but may be information on a power mode (the low power mode or the normal mode). Further, it may also be configured such that system control section 19 does not notify switching section 14, but switching section 14 detects the type of the power supply for supplying the driving power or the power mode, and selects first image processing section 15 in a case where first power supply 51 is valid (in the case of the low power mode) or selects second image processing section 16 in a case where second power supply 52 is valid (in the case of the normal mode), based on the power supply for supplying the driving power or on the power mode.

First image processing section 15 includes image data generating section 151 and learning model 152, and generates a B-mode image indicating the internal state of a subject based on the first reception signal acquired by transmitting and receiving ultrasound of a low acoustic output in accordance with an instruction from system control section 19.

Second image processing section 16 includes image data generating section 161, and generates a B-mode image indicating the internal state of a subject based on the second reception signal acquired by transmitting and receiving ultrasound of a high acoustic output in accordance with an instruction from system control section 19.

Further, although illustration is omitted, first image processing section 15 and second image processing section 16 include a digital scan converter (DSC) that performs coordinate conversion and pixel interpolation corresponding to the type of ultrasound probe 20.

Learning model 152 is formed of a neural network (for example, a convolutional neural network (CNN)), and is constructed by utilizing a publicly known machine learning algorithm (so-called deep learning). For machine learning, teaching data TD formed of a pair of low acoustic output data TD1 acquired by transmitting and receiving the first ultrasound of a low acoustic output and high acoustic output data TD2 acquired by transmitting and receiving the second ultrasound of a high acoustic output is used. Low acoustic output data TD1 and high acoustic output data TD2, which form teaching data TD, are actually acquired by transmitting and receiving the first ultrasound of a low acoustic output and the second ultrasound of a high acoustic output with respect to the same target portion.

An output result close to received data of a high acoustic output is acquired by executing learning model 152 for received data of a low acoustic output. Accordingly, by generating a B-mode image based on this output result, a B-mode image with high image quality comparable to a B-mode image acquired in the normal mode can be acquired even in the low power mode.

For example, sound ray data before image conversion (raw data), which is acquired from a reception signal of ultrasound, can be applied to teaching data TD. The data structure of the sound ray data does not depend on the type of ultrasound probe 20, such as a linear type, a sector type, and a convex type. In this case, processing by learning model 152 is performed at a stage prior to image data generating section 151 (the processing is performed by changing the order of arrangements of image data generating section 151 and learning model 152 in FIG. 3). That is, sound ray data of a low acoustic output based on the first reception signal is input, as it is, to learning model 152. An output result of learning model 152 (sound ray data after processing) is converted into image data by image data generating section 151, and a B-mode image based on the generated image data is output to display 17.

The sound ray data may be data having a two-dimensional array structure spreading in an axial direction and in an azimuth direction. In a case where ultrasound probe 20 is a 3D/4D probe, the sound ray data may be data having a three-dimensional array structure spreading in the axial direction, in the azimuth direction, and further in an elevation direction (thickness direction of the probe). The sound ray data having a two-dimensional array structure is compatible with a CNN and makes it possible to acquire a suitable output result.

Further, for example, image data after image conversion of a reception signal of ultrasound can be applied to teaching data TD. In this case, the processing by learning model 152 is performed at a stage subsequent to image data generating section 151. That is, sound ray data of a low acoustic output based on the first reception signal is converted into image data by image data generating section 151. Then, this image data is input to learning model 152, and a B-mode image based on an output result of learning model 152 (image data after processing) is output, as it is, to display 17.

Training of learning model 152, that is, generation of an adjustment value suitable for learning model 152 is performed, for example, by model training section 40.

Note that, in the present embodiment, an example is described in which model training section 40 is provided in the ultrasound diagnostic apparatus and learning model 152 is capable of learning in the ultrasound diagnostic apparatus. However, an aspect is possible in which model training section 40 is not provided in the ultrasound diagnostic apparatus and learning model 152 that has learned in advance is implemented therein. By providing model training section 40 in the ultrasound diagnostic apparatus, it is possible to improve the accuracy of an output result by learning model 152 even when learning model 152 has learned in advance. Further, by providing model training section 40 in the ultrasound diagnostic apparatus, it is also possible to use ultrasound image data acquired by ultrasound diagnosis as teaching data, and to suppress labor for inputting teaching data necessary for learning.

Further, in the present embodiment, image data generating section 151 of first image processing section 15 and image data generating section 161 of second image processing section 16 are provided, respectively, but it may be configured such that a common image data generating section is provided for first image processing section 15 and 20) second image processing section 16. In such a configuration, it is possible to configure such that the image data generating section and learning model 152 are selected in the case of the low power mode, and that the image data generating section is selected in the case of the normal mode.

Display 17 is formed of, for example, a liquid crystal display, an organic EL display, a CRT display, or the like. Display 17 displays an image based on a display signal from a display processing section (illustration is omitted) in accordance with an instruction from system control section 19.

Communication section 18 includes, for example, various interfaces such as a network interface card (NIC), a modulator-demodulator (MODEM), and a universal serial bus (USB). It is also possible to apply a communication interface for short-distance wireless communication, such as near field communication (NFC) and Bluetooth (registered trademark), to communication section 18. CPU 191 transmits and receives various kinds of information to and from an external apparatus (for example, a personal computer and a cloud storage on the Internet) connected to a communication network, such as a wired/wireless local area network (LAN), via communication section 18.

System control section 19 performs overall control of ultrasound diagnostic apparatus 1 by controlling operation input section 11, transmission section 12, reception section 13, switching section 14, first image processing section 15, second image processing section 16, display 17, and model training section 40 in accordance with respective functions.

System control section 19 includes central processing unit (CPU) 191 as an arithmetic/control apparatus, read-only memory (ROM) 192 as a main storage apparatus, random access memory (RAM) 193, and the like. ROM 192 stores a basic program and basic setting data. Further, ROM 192 stores an ultrasound diagnostic program to be executed during diagnosis. CPU 191 performs centralized control of operation of each functional block of ultrasound 40) diagnostic apparatus main body 10 (transmission section 12, reception section 13, switching section 14, first image processing section 15, second image processing section 16, display 17, and model training section 40) by reading a program corresponding to the content of processing from ROM 192, developing the program to RAM 193, and executing the developed program.

In the present embodiment, the functions of the respective functional blocks are realized by cooperation between respective pieces of hardware forming the functional blocks and system control section 19. Note that, some or all of the functions of the respective functional blocks may be realized by execution of programs by system control section 19.

Figure 4:
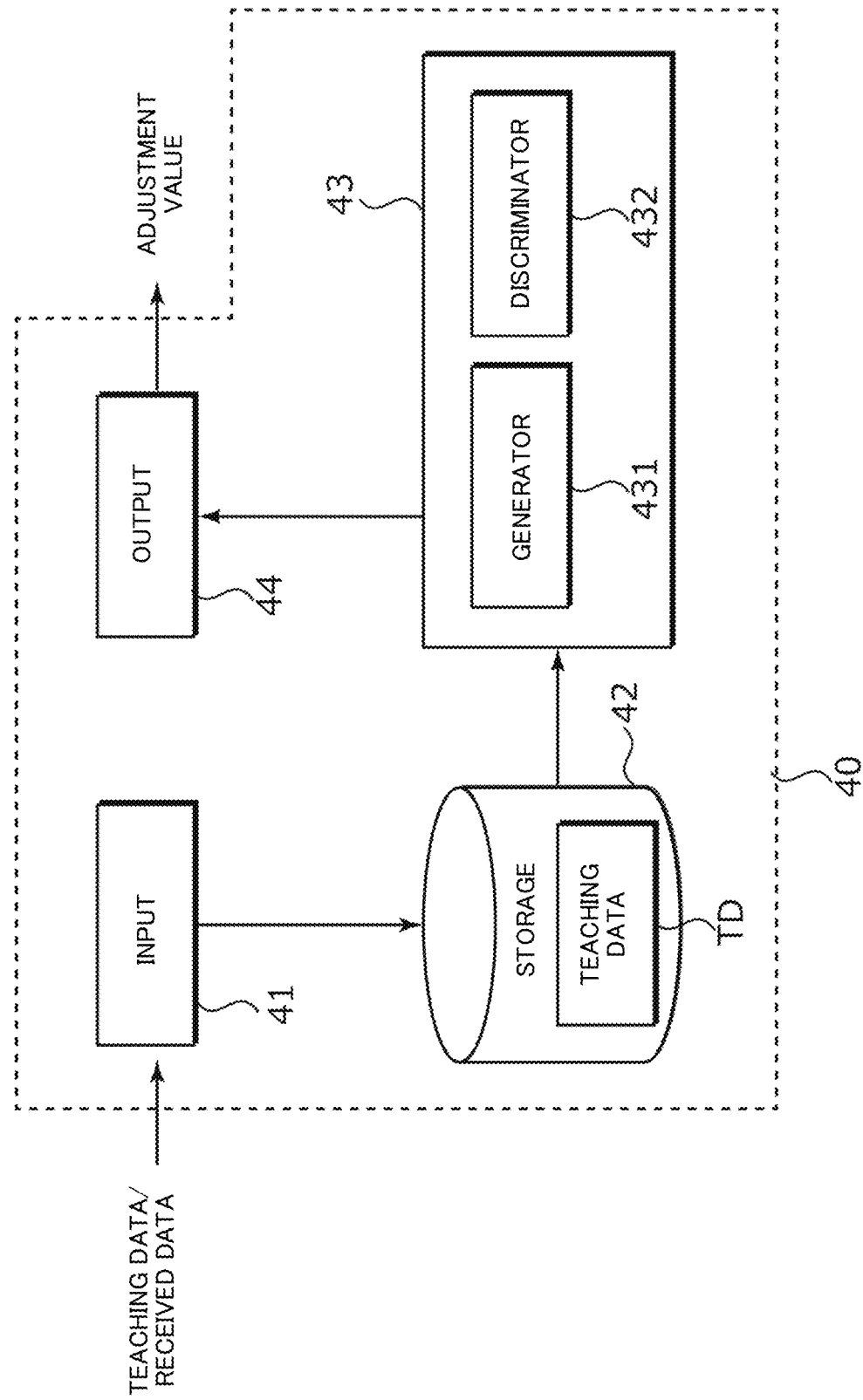
FIG. 4 illustrates a specific configuration of a model training section.
Figure 5:
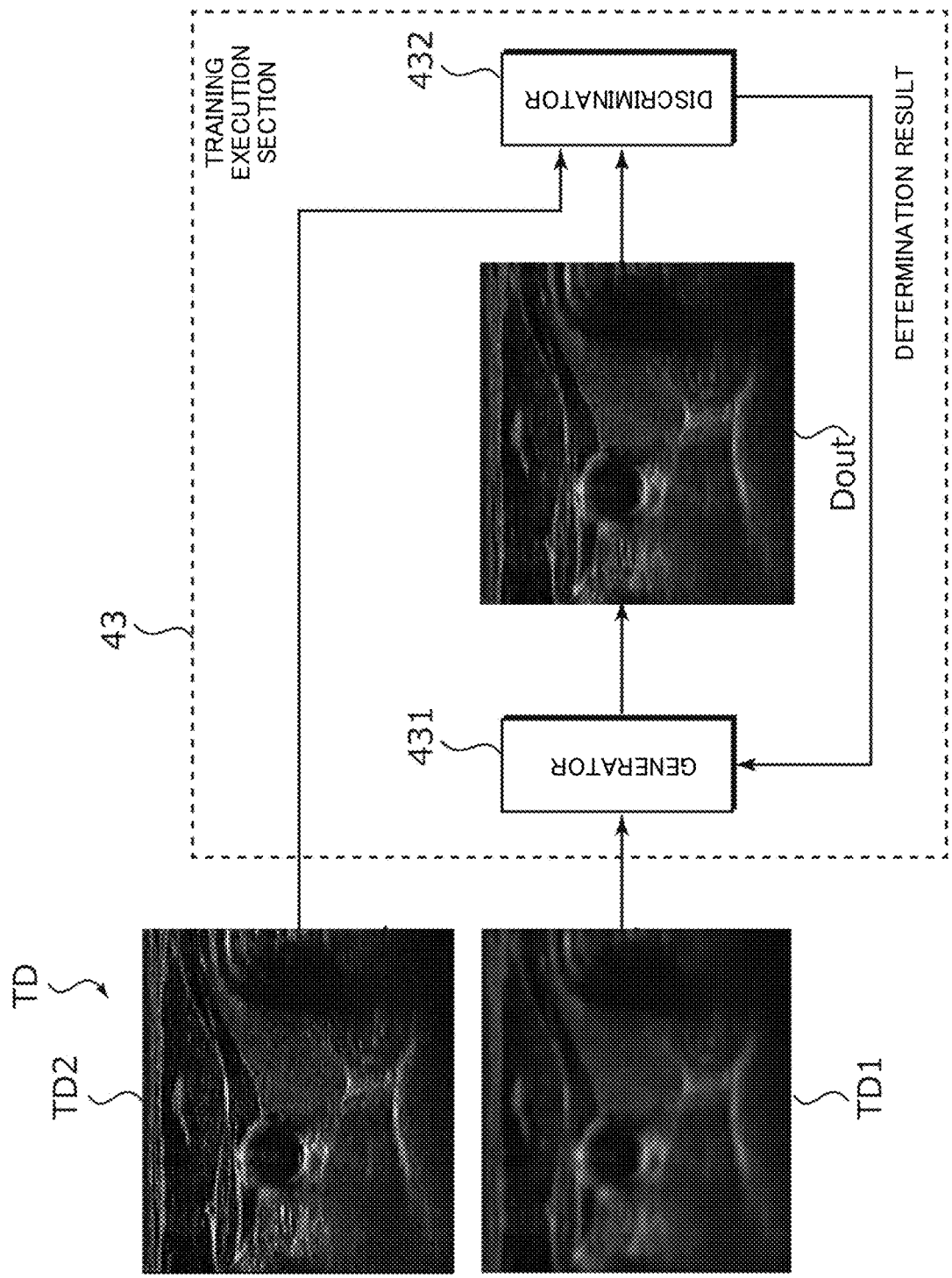
FIG. 5 illustrates contents of processing of a training execution section.

FIG. 4 illustrates a specific configuration of model training section 40. FIG. 5 illustrates contents of processing of a training execution section.

As illustrated in FIG. 4, model training section 40 includes input 41, storage 42, training execution section 43, and output 44.

Input 41 acquires teaching data TD formed of the pair of low acoustic output data TD1 (example) and high acoustic output data TD2 (answer). In the present embodiment, input 41 generates teaching data TD from the first reception signal acquired by transmitting and receiving the first ultrasound of a low acoustic output and the second reception signal acquired by transmitting and receiving the second ultrasound of a high acoustic output (teaching data generating section). Note that, input 41 may also acquire teaching data TD stored in a cloud storage on a network via communication section 18.

Teaching data TD is generated based on reception signals acquired by alternately and continuously transmitting and receiving the first ultrasound of a low acoustic output and the second ultrasound of a high acoustic output with respect to the same object, for example. Specifically, low acoustic output data TD1 is generated from the first reception signal acquired by transmitting and receiving the first ultrasound, and high acoustic output data TD2 is generated from the second reception signal acquired by transmitting and receiving the second ultrasound.

At this time, the first reception signal and the second reception signal may be acquired alternately in units of frames or may be acquired alternately in units of sound rays. In the case of the acquisition in units of frames, it is possible to simplify ultrasound transmission and reception processing in comparison with the case of the acquisition in units of sound rays. In the case of the acquisition in units of sound rays, it is possible to suppress a time lag between data serving as the pair for teaching data TD as much as possible in comparison with the case of the acquisition in units of frames, and it is possible to generate suitable teaching data TD.

Storage 42 stores teaching data TD acquired by input 41. Teaching data TD used for training may be overwritten as appropriate in a case where teaching data TD is newly acquired by input 41.

Note that, teaching data TD generated by input 41 may be transferred to a cloud storage on a network via communication section 18 and stored therein. In this case, teaching data TD can be shared with another ultrasound diagnostic apparatus 1 in which learning model 152 is implemented, and an enormous amount of teaching data TD necessary for training learning model 152 can be easily prepared.

As illustrated in FIG. 5, training execution section 43 includes a neural network similar to learning model 152, and optimizes an adjustment value of the neural network by machine learning using teaching data TD. Specifically, training execution section 43 optimizes an adjustment value (parameter) of generator 431 such that high acoustic output data TD2 (answer of teaching data TD) is output when low acoustic output data TD1 (example of teaching data TD) is input to generator 431. FIG. 5 illustrates a case in which image data after image conversion is applied to teaching data TD.

For example, generative adversarial networks (GAN) including generator 431 and discriminator 432 can be applied to training execution section 43. Generator 431 is formed of a neural network similar to learning model 152 and generates output data Dout from low acoustic output data TD1. Discriminator 432 compares output data Dout with high acoustic output data TD2 and determines authenticity of output data Dout. An adjustment value of generator 431 is optimized by back-propagating a determination result of discriminator 432 to generator 431 and discriminator 432, and alternately causing generator 431 and discriminator 432 to contest with each other.

An adjustment value of generator 431 is output from output 44 and is reflected in learning model 152. In this manner, training of learning model 152 is performed.

Figure 6:
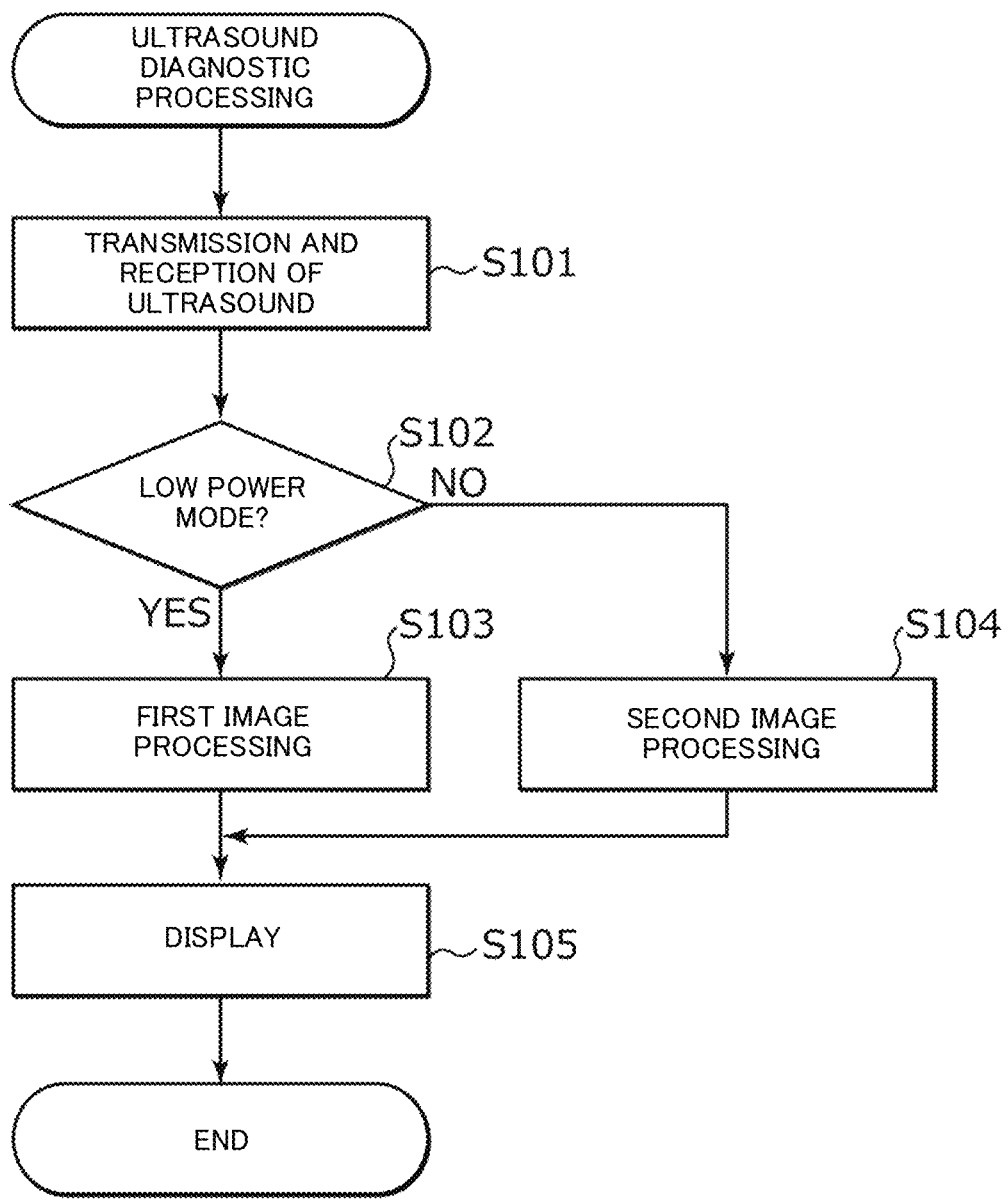
FIG. 6 is a flowchart illustrating an example of ultrasound diagnostic processing in the ultrasound diagnostic apparatus.

FIG. 6 is a flowchart illustrating an example of ultrasound diagnostic processing in ultrasound diagnostic apparatus 1. This processing is realized, for example, by CPU 191 executing a predetermined program stored in ROM 192 as a diagnostic mode is validated in ultrasound diagnostic apparatus 1. The validation of the diagnostic mode is performed, for example, by mode selection in operation input section 11.

In step S101, system control section 19 causes transmission and reception of ultrasound corresponding to the operation mode (low power mode/normal mode). Specifically, system control section 19 controls transmission section 12 such that the first ultrasound or the second ultrasound is transmitted from ultrasound probe 20, and controls reception section 13 such that a reception signal corresponding to reflection ultrasound (ultrasonic echo) received by ultrasound probe 20 is acquired.

In step S102, system control section 19 determines whether the operation mode is the low power mode. In a case where the operation mode is the low power mode ("YES" in step S102), the processing proceeds to processing of step S103. In a case where the operation mode is not the low power mode, that is, in a case where the operation mode is the normal mode ("NO" in step S102), on the other hand, the processing proceeds to processing of step S104.

In step S103, system control section 19 controls switching section 14 such that first image processing section 15 is selected, and causes first image processing to be executed. In step S103, a B-mode image is generated based on the first reception signal acquired by transmitting and receiving the first ultrasound. Specifically, sound ray data (or image data acquired by image conversion of sound ray data) of the first reception signal is input to learning model 152, and a B-mode image is generated based on an output result of learning model 152 and is output.

Since learning model 152 is formed of a neural network and is constructed by machine learning using teaching data TD formed of the pair of low acoustic output data TD1 and high acoustic output data TD2, an image quality equivalent to that of a B-mode image acquired by transmitting and receiving the second ultrasound of a high acoustic output is realized in the B-mode image generated based on the output result of learning model 152.

In step S104, system control section 19 controls switching section 14 such that second image processing section 16 is selected, and causes second image processing to be executed. In step S104, sound ray data of the second reception signal acquired by transmitting and receiving the second ultrasound is utilized, as it is, to be image-converted, and a B-mode image is generated.

In step S105, system control section 19 controls display 17 such that a display image for diagnosis is displayed based on the generated image data. Even in the low power mode, a user is capable of performing a diagnosis with an ultrasound image with high image quality equivalent to that in the normal mode.

Thus, ultrasound diagnostic apparatus 1 according to the embodiment is an ultrasound diagnostic apparatus that generates and displays an ultrasound image based on a reception signal corresponding to reflection ultrasound reflected in a subject, and includes transmission section 12 and reception section 13 (transceiver) that transmit and receive first ultrasound of a low acoustic output and second ultrasound of a high acoustic output: and first image processing section 15 that generates the ultrasound image based on a first reception signal acquired by transmitting and receiving the first ultrasound. First image processing section 15 includes learning model 152, and generates the ultrasound image based on an output result of learning model 152 when the first reception signal is input. Learning model 152 is formed of a neural network and is acquired by machine learning using teaching data TD formed of a pair of low acoustic output data TD1 acquired by transmitting and receiving the first ultrasound and high acoustic output data TD2 acquired by transmitting and receiving the second ultrasound.

Further, the ultrasound diagnostic method according to the embodiment is an ultrasound diagnostic method in which a diagnosis is performed with an ultrasound image based on a reception signal corresponding to reflection ultrasound reflected in a subject. The ultrasound diagnostic method includes: transmitting and receiving first ultrasound of a low acoustic output or second ultrasound of a high acoustic output (step S101 in FIG. 6): and generating the ultrasound image based on a first reception signal acquired by transmitting and receiving the first ultrasound (step S103 in FIG. 6). In the generating, the ultrasound image is generated by utilizing learning model 152 and based on an output result of learning model 152 when the first reception signal is input. Learning model 152 is formed of a neural network and is acquired by machine learning using teaching data TD formed of a pair of low acoustic output data TD1 acquired by transmitting and receiving the first ultrasound and high acoustic output data TD2 acquired by transmitting and receiving the second ultrasound.

Further, the program according to the embodiment is a program that causes a computer of ultrasound diagnostic apparatus 1 to execute predetermined processing. Ultrasound diagnostic apparatus 1 generates and displays an ultrasound image based on a reception signal corresponding to reflection ultrasound reflected in a subject. The predetermined processing includes: transmitting and receiving first ultrasound of a low acoustic output or second ultrasound of a high acoustic output (step S101 in FIG. 6): and generating the ultrasound image based on a first reception signal acquired by transmitting and receiving the first ultrasound (step S103 in FIG. 6). In the generating, the ultrasound image is generated by utilizing learning model 152 and based on an output result of learning model 152 when the first reception signal is input. Learning model 152 is formed of a neural network and is acquired by machine learning using teaching data TD formed of a pair of low acoustic output data TD1 acquired by transmitting and receiving the first ultrasound and high acoustic output data TD2 acquired by transmitting and receiving the second ultrasound.

This program is provided via, for example, a computer-readable portable recording medium (including an optical disk, a magneto-optical disk, and a memory card) storing the program therein. Further, for example, this program can also be provided by being downloaded via a network from a server that holds the program.

According to ultrasound diagnostic apparatus 1, the ultrasound diagnostic method, and the program according to the embodiment, it is possible to acquire an ultrasound image with high image quality necessary for a diagnosis even at low acoustic output, and it is possible to achieve a reduction in the power consumption and size of the apparatus.

Further, ultrasound diagnostic apparatus 1 includes second image processing section 16 that generates the ultrasound image based on a second reception signal acquired by transmitting and receiving the second ultrasound: and switching section 14 that selects first image processing section 15 in a case where the reception signal is the first reception signal, and that selects the second image processing section in a case where the reception signal is the second reception signal. Thus, the acoustic output of ultrasound can be used by appropriately switching between a low acoustic output and a high acoustic output, and image processing suitable for each acoustic output is performed so that convenience of ultrasound diagnostic apparatus 1 improves.

Further, ultrasound diagnostic apparatus 1 includes first power supply 51 formed of a battery: and second power supply 52 that receives power supply from an external power supply. Transmission section 12 and reception section 13 (transceiver) transmit and receive the first ultrasound in a case where driving power is supplied from first power supply 51, and transmit and receive the second ultrasound in a case where the driving power is supplied from second power supply 52. Thus, an acoustic output of ultrasound is selected in accordance with the supply source of the driving power, and image processing suitable for the acoustic output is performed so that the convenience of ultrasound diagnostic apparatus 1 further improves.

Further, in ultrasound diagnostic apparatus 1, teaching data TD is sound ray data before image conversion, and the sound ray data spreads in an axial direction and in an azimuth direction. Since this two-dimensional data has a two-dimensional array structure of the number of sampling points of sound rays in the axial direction×the number of sound rays in the azimuth direction orthogonal to the sound rays, a CNN proven in image processing can be applied to learning model 152.

Further, in ultrasound diagnostic apparatus 1, teaching data TD may further spread in an elevation direction. In this case, it is possible to deal with a case where a probe having a matrix array structure, a 3D/4D probe of a mechanical oscillation method or the like is used as ultrasound probe 20.

Further, in ultrasound diagnostic apparatus 1, teaching data TD is image data after image conversion of the reception signal. In this case, a CNN proven in image processing can be applied to learning model 152.

Further, ultrasound diagnostic apparatus 1 includes model training section 40 that trains learning model 152. Model training section 40 includes input 41 that acquires teaching data TD: training execution section 43 that includes a neural network similar to learning model 152 and optimizes an adjustment value of the neural network by using teaching data TD: and output 44 that outputs the adjustment value of the neural network. The adjustment value is reflected in learning model 152. Thus, training of learning model 152 can be performed in ultrasound diagnostic apparatus 1, and accuracy of learning model 152 can be easily improved.

Further, in ultrasound diagnostic apparatus 1, training execution section 43 includes generator 431 that is formed of the neural network and generates output data from low acoustic output data TD1: and discriminator 432 that compares the output data with high acoustic output data TD2 and determines authenticity of the output data. The adjustment value is optimized while a determination result of discriminator 432 is back-propagated to generator 431 and discriminator 432 and generator 431 and discriminator 432 are alternately caused to contest with each other. Thus, it is possible to apply a technique of publicly known GAN and to easily optimize an adjustment value of generator 431.

Further, in ultrasound diagnostic apparatus 1, input 41 includes a teaching data generating section that generates teaching data TD from the first reception signal and the second reception signal. Thus, it is possible not only to train learning model 152 but also to generate teaching data TD in ultrasound diagnostic apparatus 1, and the accuracy of learning model 152 can be easily improved.

Further, in ultrasound diagnostic apparatus 1, input 41 (teaching data generating section) generates teaching data TD based on the first reception signal and the second reception signal that are continuously acquired in units of frames. In this case, it is possible to simplify ultrasound transmission and reception processing.

Further, in ultrasound diagnostic apparatus 1, input 41 (teaching data generating section) generates teaching data TD based on the first reception signal and the second reception signal that are continuously acquired in units of sound rays. In this case, it is possible to suppress a time lag between data serving as the pair for teaching data TD as much as possible, and it is possible to generate suitable teaching data TD.

Further, in ultrasound diagnostic apparatus 1, teaching data TD generated by input 41 (teaching data generating section) is transferred to a cloud storage on a network. Thus, teaching data TD can be shared with another ultrasound diagnostic apparatus 1 in which learning model 152 is implemented, and convenience improves.

Further, in ultrasound diagnostic apparatus 1, input 41 acquires teaching data TD from a cloud storage on a network. Thus, an enormous amount of teaching data TD necessary for training learning model 152 can be easily acquired, and the accuracy of learning model 152 can be increased.

Although the invention made by the present inventor has been described above based on an embodiment, the present invention is not limited to the above embodiment and can be changed without departing from the gist of the invention.

For example, although a case where a CNN is applied to learning model 152 has been described in the embodiment, a neural network based on a publicly known technique such as a super-resolution technique and sharpening filter processing, which enhance the image quality of a blurred image, and applicable to an image processing task may also be applied.

Further, in the embodiment, a case where the second ultrasound of a high acoustic output is transmitted and received in the normal mode has been described. However, in a case where an ultrasound image does not need to have high image quality, for example, in the case of confirmation of a diagnosis target portion or the like, it may also be configured such that the first ultrasound of a low acoustic output is transmitted and received in the normal mode to thereby achieve power saving.

Further, although a case where learning model 152 is trained by model training section 40 implemented in ultrasound diagnostic apparatus 1 has been described in the embodiment, learning model 152 may also be trained by an external computer (model training apparatus) having a functional configuration similar to that of model training section 40.

Furthermore, training execution section 43 is not necessarily formed of GAN made of two CNNs (generator and discriminator), but may be formed of a single CNN. In this case, for example, a U-shaped CNN termed as a publicly known U-Net may be applied, or a CNN such as a VGG16, which has already learned with a large-scale image dataset termed as a publicly known ImageNet, may be subjected to transfer learning and fine-tuned to a CNN with a suitable shape for model training section 40.

Although embodiments of the present invention have been described and illustrated in detail, the disclosed embodiments are made for purpose of illustration and example only and not limitation. The scope of the present invention should be interpreted by terms of the appended claims.

What is claimed is:

1. An ultrasound diagnostic apparatus that generates and displays an ultrasound image based on a reception signal corresponding to reflection ultrasound reflected in a subject, the ultrasound diagnostic apparatus comprising:
   a transceiver that transmits and receives first ultrasound of a low acoustic output and second ultrasound of a high acoustic output; and
   a first hardware processor that generates the ultrasound image based on a first reception signal acquired by transmitting and receiving the first ultrasound;
   a second hardware processor that generates the ultrasound image based on a second reception signal acquired by transmitting and receiving the second ultrasound;
   a first power supply formed of a battery;
   a second power supply that receives power from an external power supply; and
   a third hardware processor, wherein the transceiver transmits and receives the first ultrasound and the third hardware processor selects the first hardware processor in a case where the driving power is supplied from the first power supply, and the transceiver transmits and receives the second ultrasound and the third hardware processor selects the second hardware processor in a case where the driving power is supplied from the second power supply, wherein
   the first hardware processor includes a learning model formed of a neural network utilizing a machine learning algorithm,
   the learning model is acquired by machine learning using teaching data formed of a pair of low acoustic output data acquired by transmitting and receiving the first ultrasound and high acoustic output data acquired by transmitting and receiving the second ultrasound, and
   the teaching data is generated based on reception signals acquired by alternately and continuously transmitting the first ultrasound and the second ultrasound with respect to the same object.

2. The ultrasound diagnostic apparatus according to claim 1, wherein the third hardware processor selects the first hardware processor in a case where a power mode is a low power mode.

3. The ultrasound diagnostic apparatus according to claim 1, wherein the teaching data is sound ray data before image conversion, the sound ray data spreading in an axial direction and in an azimuth direction.

4. The ultrasound diagnostic apparatus according to claim 3, wherein the teaching data further spreads in an elevation direction.

5. The ultrasound diagnostic apparatus according to claim 1, wherein the teaching data is image data after image conversion of the reception signal.

6. The ultrasound diagnostic apparatus according to claim 1, further comprising:
a fourth hardware processor that trains the learning model; and
a first memory that stores a neural network similar to the learning model, wherein
the fourth hardware processor
acquires the teaching data,
optimizes an adjustment value of the neural network by using the teaching data, and
outputs the adjustment value of the neural network, wherein
the adjustment value is reflected in the learning model.

7. The ultrasound diagnostic apparatus according to claim 6, wherein
the fourth hardware processor includes:
a generator that is formed of the neural network and generates output data from the low acoustic output data, and
a discriminator that compares the output data with the high acoustic output data and determines authenticity of the output data, wherein
the adjustment value is optimized while a determination result of the discriminator is back-propagated to the generator and the discriminator and the generator and the discriminator are alternately caused to contest with each other.

8. The ultrasound diagnostic apparatus according to claim 6, wherein the fourth hardware processor generates the teaching data based on the reception signals, which are continuously acquired in units of frames.

9. The ultrasound diagnostic apparatus according to claim 6, wherein the fourth hardware processor generates the teaching data based on the reception signals, which are continuously acquired in units of sound rays.

10. The ultrasound diagnostic apparatus according to claim 6, wherein the teaching data generated by the fourth hardware processor is transferred to a cloud storage on a network.

11. The ultrasound diagnostic apparatus according to claim 6, wherein the fourth hardware processor acquires the teaching data from a cloud storage on a network.

12. A model training apparatus that trains the learning model to be implemented in the ultrasound diagnostic apparatus according to claim 1, the model training apparatus comprising:
a fifth hardware processor; and
a second memory that stores a neural network similar to the learning model, wherein
the fifth hardware processor
acquires the teaching data,
optimizes an adjustment value of the neural network by using the teaching data, and
outputs the adjustment value of the neural network.

13. The ultrasound diagnostic apparatus according to claim 1, wherein the first hardware processor performs image processing using the learning model on the ultrasound image based on the first reception signal to increase an image quality of the ultrasound image based on the first reception signal.

14. The ultrasound diagnostic apparatus according to claim 1, wherein
the first hardware processor generates the ultrasound image based on the first reception signal using an image generator;
the second hardware processor generates the ultrasound image based on the second reception signal using the image generator or another image generator, wherein the ultrasound image based on the first reception signal has a lower image quality than the ultrasound image based on the second reception signal; and
the first hardware processor performs image processing using the learning model to increase an image quality of the ultrasound image based on the first reception signal.

15. The ultrasound diagnostic apparatus according to claim 1, wherein
the transmission voltage of the first ultrasound is smaller than that of the second ultrasound.

16. An ultrasound diagnostic method in which a diagnosis is performed with an ultrasound image based on a reception signal corresponding to reflection ultrasound reflected in a subject, the ultrasound diagnostic method comprising:
transmitting and receiving first ultrasound of a low acoustic output or second ultrasound of a high acoustic output; and
generating, using a first hardware processor, the ultrasound image based on a first reception signal acquired by transmitting and receiving the first ultrasound, wherein the ultrasound image is generated by utilizing a learning model and based on an output result of the learning model when the first reception signal is input, the learning model being formed of a neural network;
generating, using a second hardware processor, the ultrasound image based on a second reception signal acquired by transmitting and receiving the second ultrasound; and
selecting the first hardware processor to generate the ultrasound image based on the first reception signal or the second hardware processor to generate the ultrasound image based on the second reception signal,
in a case where driving power is supplied from a first power supply formed of a battery, the step of transmitting and receiving includes transmitting and receiving the first ultrasound and the step of selecting includes selecting the first hardware processor, and
in a case where the driving power is supplied from a second power supply that receives power from an external power supply, the step of transmitting and receiving includes transmitting and receiving the second ultrasound and the step of selecting includes selecting the second hardware processor,
wherein the learning model is acquired by machine learning using teaching data formed of a pair of low acoustic output data acquired by transmitting and receiving the first ultrasound and high acoustic output data acquired by transmitting and receiving the second ultrasound, and
the teaching data is generated based on reception signals acquired by alternately and continuously transmitting the first ultrasound and the second ultrasound with respect to the same object.

17. A non-transitory computer-readable recording medium storing therein a program that causes a computer of an ultrasound diagnostic apparatus to execute predetermined processing, the ultrasound diagnostic apparatus generating and displaying an ultrasound image based on a reception signal corresponding to reflection ultrasound reflected in a subject, the predetermined processing comprising:

- transmitting and receiving first ultrasound of a low acoustic output or second ultrasound of a high acoustic output;
- generating, using a first hardware processor, the ultrasound image based on a first reception signal acquired by transmitting and receiving the first ultrasound, wherein the ultrasound image is generated by utilizing a learning model and based on an output result of the learning model when the first reception signal is input, the learning model being formed of a neural network utilizing a machine learning algorithm;
- generating, using a second hardware processor, the ultrasound image based on a second reception signal acquired by transmitting and receiving the second ultrasound; and
- selecting the first hardware processor to generate the ultrasound image based on the first reception signal or the second hardware processor to generate the ultrasound image based on the second reception signal,
- in a case where driving power is supplied from a first power supply formed of a battery, the step of transmitting and receiving includes transmitting and receiving the first ultrasound and the step of selecting includes selecting the first hardware processor, and
- in a case where the driving power is supplied from a second power supply that receives power from an external power supply, the step of transmitting and receiving includes transmitting and receiving the second ultrasound and the step of selecting includes selecting the second hardware processor,
- wherein the learning model is acquired by machine learning using teaching data formed of a pair of low acoustic output data acquired by transmitting and receiving the first ultrasound and high acoustic output data acquired by transmitting and receiving the second ultrasound, and
- the teaching data is generated based on reception signals acquired by alternately and continuously transmitting the first ultrasound and the second ultrasound with respect to the same object.

* * * * *